United States Patent [19]

Lindskog et al.

[11] Patent Number: 5,327,903
[45] Date of Patent: Jul. 12, 1994

[54] APPARATUS FOR DIAGNOSING PERIODONTITIS

[75] Inventors: Sven Lindskog, Stockholm; Leif Blomlöf, Lidingö, both of Sweden

[73] Assignees: Biora AB; Bioapatite AB, both of Malmö, Sweden

[21] Appl. No.: 910,148
[22] PCT Filed: Jan. 28, 1991
[86] PCT No.: PCT/SE91/00062
 § 371 Date: Aug. 21, 1992
 § 102(e) Date: Aug. 21, 1992
[87] PCT Pub. No.: WO91/11141
 PCT Pub. Date: Aug. 8, 1991

[30] Foreign Application Priority Data

Jan. 29, 1990 [SE] Sweden .................. 9000305-4

[51] Int. Cl.$^5$ .................................. A61B 5/00
[52] U.S. Cl. ......................... 128/736; 128/776; 433/32; 433/72; 374/142
[58] Field of Search .............. 128/736, 774, 776, 777; 433/27, 72, 141, 32; 33/512, 513, 514; 374/112, 116, 142, 155

[56] References Cited

U.S. PATENT DOCUMENTS

| | | | |
|---|---|---|---|
| 4,499,906 | 2/1985 | Wohlgemuth et al. | 128/776 |
| 4,665,621 | 5/1987 | Ackerman et al. | 33/513 |
| 4,773,766 | 9/1988 | Nagasaka et al. | 324/124 |
| 4,791,940 | 12/1988 | Hirschfeld et al. | 128/776 |
| 4,823,809 | 4/1989 | Gott, Jr. et al. | 128/776 |
| 4,832,599 | 5/1989 | Kung | 433/32 |
| 4,841,987 | 6/1989 | Brown et al. | 128/777 |
| 4,904,184 | 2/1990 | Murphy et al. | 433/72 |
| 4,962,765 | 10/1990 | Kung et al. | 128/736 |
| 5,044,951 | 9/1991 | Sheridan | 433/72 |
| 5,078,137 | 1/1992 | Edell et al. | 128/635 |

FOREIGN PATENT DOCUMENTS 0296520 12/1988 European Pat. Off. .

OTHER PUBLICATIONS

"The Temperature of the Periodontal Pockets", by Sabyasachi Mukherjee, *Journal of Clinical Periodontology*, 8, pp. 17 to 20 (1981).

*Primary Examiner*—Stephen C. Pellegrino
*Assistant Examiner*—Guy V. Tucker
*Attorney, Agent, or Firm*—Burns, Doane, Swecker & Mathis

[57] ABSTRACT

An apparatus for diagnosing an inflammatory condition relating to periodontitis made up of a probe with sensors for measuring temperature within a periodontal pocket. The apparatus further comprises a graduated scale for measuring the depth of the periodontal pocket. Also provided is equipment for recording the temperature difference between the bottom and the mouth of the periodontal pocket.

4 Claims, 5 Drawing Sheets

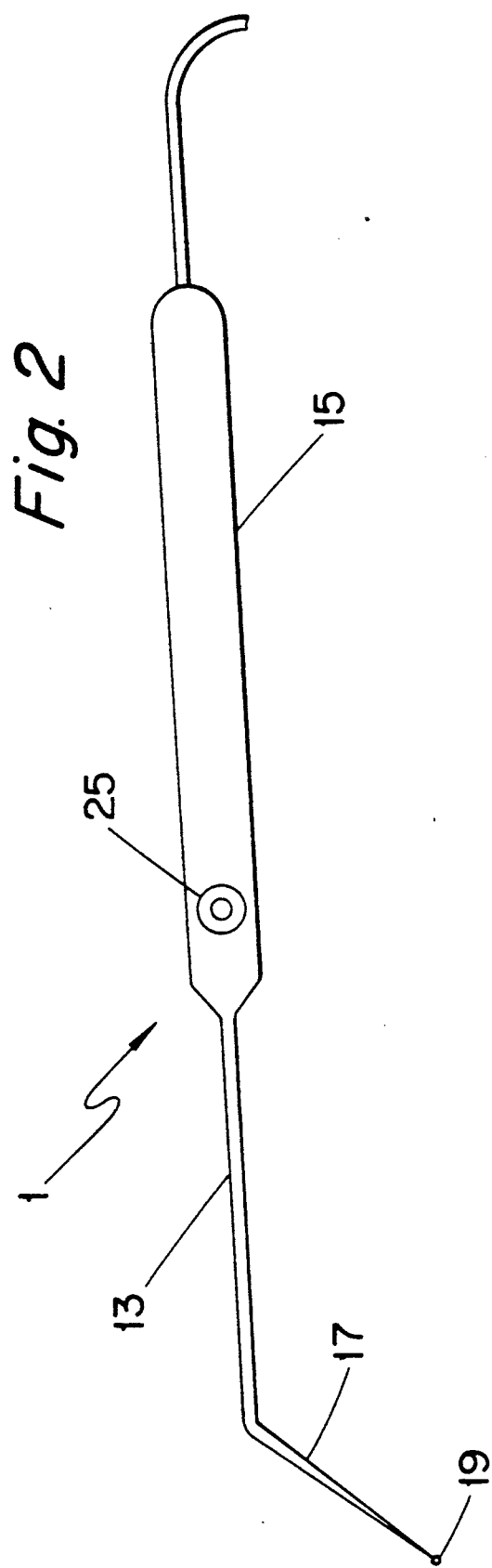
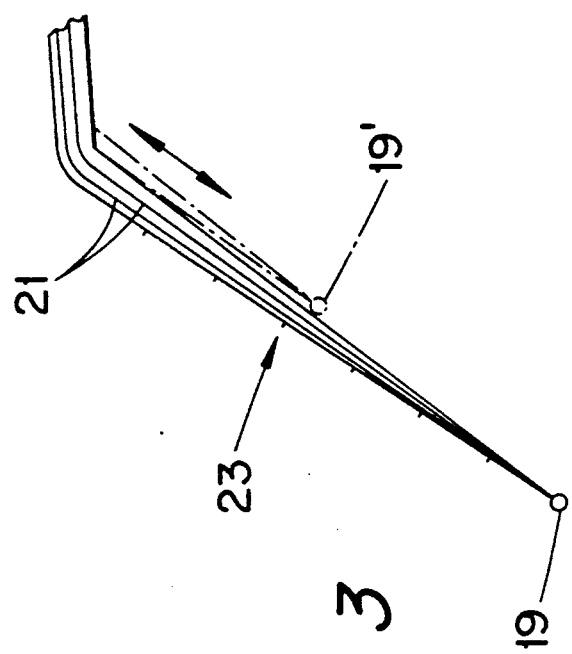

APPARATUS FOR DIAGNOSING PERIODONTITIS

BACKGROUND OF THE INVENTION

1. Field of the Invention

The present invention relates to an apparatus or diagnosing inflammatory conditions in connection with periodontitle, and the invention also involves a process for such diagnosis.

2. Description of Related Art

The loosening of teeth (periodontitis) is a bacterially caused inflammation in the attachment apparatus of the tooth (periodontium) which, if left untreated results in decomposition of the bone around the tooth (resorption) and of the tooth loosening its anchorage, the anchorage being ultimately lost. Periodontitis shall primarily be prevented by good oral hygiene but may also, after being established, be treated. This treatment will mainly be directed to interrupt the progress of the disease.

Practically all adults are to a greater or lesser degree subjected to the disease, and approximately 10% of the population in the industrialized world develop severe periodontitis resulting in partial or total loss of the teeth.

Periodontitis is initially a disease which to the patient lacks symptoms. However, the dentist can see early signs of an incipient disease development. The gum around the teeth become red, swollen and bleed easily, i.e. show signs of an inflammation. Simultaneously the pocket between tooth and gum will be subject to increased depth. In this pocket additional bacteria will accumulate and proliferate (plaque). Gradually the bacteria will calcify and calculus will form on the teeth. Synchronously with the formation of plaque the inflamation spreads in the attachment apparatus of the tooth and the bone surrounding the root of the tooth starts to decompose.

The methods available to the dentist to diagnose periodontitis is measuring the depth of the periodontal pocket around the tooth and registering the tendency for bleeding connection herewith. However, this does not give a full measure of the degree of inflamation in the attachment apparatus of the tooth. Above all these measures give little guidance for judging how the disease will develop. They rather reflect what has already taken place.

One of the greatest problem in the treatment of periodontitis is to be able to predict around what teeth the periodontitis activity will increase. It has been found that the loss of supporting tissue around the teeth in periodontitis fluctuates, i.e. periods of low disease activity succeed periods of high activity. Early signs of this can be seen in the degree of inflammation in the environment of the teeth. An incipient increase of the degree of inflammation should be treated as soon as possible in order to save as much as possible of the anchorage of the tooth. The traditional methods (depth of periodontal pocket and bleeding tendency) in order to estimate this condition are not reliable. A deep periodontal pocket does not necessarily mean that the periodontal process is active. A healing process may have started in the same manner a shallow periodontal pocket may not mean that the periodontal disease is inactive. Also a deep pocket has once been shallow and it is very important to be able to predict which periodontal pockets are subject to deepening.

The cardinal symptoms of a topical inflammatory condition is calor (temperature increase), dolor (pain), rubor (redness) and tumor (swelling). Out of these the redness (bleeding in the periodontal pocket) and the swelling (in combination with decomposition of alveolar bone, i.e. measuring depth of periodontal pocket) have traditionally been used to diagnose periodontitis. However, these symptoms of periodontitis are not reliable measures for estimating the activity of the disease. Furthermore, it is not possible to estimate bleeding quantitatively. These traditional methods, measuring of pocket depth and bleeding tendency, to judge the activity of the periodontal process often give misleading results, particularly in an early stage of an active period. A deep periodontal pocket which is bleeding does not always mean that the process is active.

The use of temperature as a measurement for the activity of periodontitis is based on the fact that an inflammatory process in view of increased flow of blood results in an early temperature increase (before the depth of the periodontal pocket has increased). However, in the mouth the temperature varies between different areas. The gum is warmer the deeper in the oral cavity the measurement le made (32° C. to 37° C.). An absolute temperature scale to estimate the degree of inflammation is thus not possible to define. However, the surface temperature in the opening of the periodontal pocket is not affected by a possible inflammation at the bottom the periodontal pocket.

SUMMARY OF THE INVENTION

The present invention has for an object to provide an apparatus by means of which inflammatory conditions in connection with periodontitis can be diagnosed in a simple and reliable manner.

Another object of the invention is to provide a process for diagnosing the degree of inflammatory condition connection with periodontitis, which process is based on an estimation of the exterior conditions around a so called periodontal pocket.

For these and other objects which will be clear from the following disclosure the invention provides for an apparatus for diagnosing periodontitis in view of its inflammatory aspect, said apparatus comprising means for measuring and recording temperature in connection with a periodontal pocket. The apparatus for such diagnosis is provided with a measuring means with a graduated scale for measuring the depth of the periodontal pocket and in association herewith also provided with means for measuring and recording the temperature difference between the bottom and the mouth of the periodontal pocket.

The apparatus means for temperature measurement suitably constituted by a probe which is connected to the measuring means in such a manner that the depth of the periodontal pocket can be recorded in connection with measuring the temperature at its bottom.

The temperature sensor or transducer, which is suitably positioned at the free end of the probe, can be of different types, of which examples are thermoelements, thermistors, semiconductor diodes and resistance transducers.

In a particularly preferred embodiment of the apparatus according to the present invention the probe and the measuring means are assembled to one unit. In an alternative embodiment of the apparatus according to the invention said means for temperature measurement may comprise a probe with two transducers displacable relative to each other, the apparatus also including a measuring means with a graduated scale for measuring the depth of the periodontal pocket. One end of the probe being permanently connected to the measuring means at its free end, whereas the other transducer is movable along the scale so that the temperature difference between the bottom and the mouth of the periodontal pocket can be registered at the same time as the pocket depth is measured.

It is obvious for a man skilled in the art that the temperature simultaneously can be monitored at various levels of a tooth pocket by an array of sensors, or transducers.

The invention also provides for process for diagnosing inflammatory conditions in connection with periodontitis, said process being based on considering the exterior conditions around a so called periodontal pocket. This process comprises the steps:

a) measuring the depth of the periodontal pocket, i.e. the distance between the bottom and the mouth of the pocket;

b) measuring the temperature difference between the bottom and mouth of the periodontal pocket; and c) determining-the degree and development of the periodontitis in dependence of the parameters measured under step a) and step b).

In connection with the techniques according to the present invention it can be generally said that a temperature increase at the bottom of the periodontal pocket, more precisely a temperature difference of more than about 0.5° C. between the mouth and bottom of the periodontal pocket, constitutes an early sign of the fact that the periodontal process is entering an active stage. A temperature difference of more than about 1° C. shows that the process is established. The present invention thus provides for reliable diagnostic techniques which are based on simultaneous measurement of the temperature difference between the bottom and the mouth of the pocket and the depth of the pocket, and through said techniques one may thus verify whether the periodontal process resides in an active stage and whether said process is established.

BRIEF DESCRIPTION OF THE DRAWINGS

The invention will in the following be further described by non-limiting examples in conjunction with the appended drawings, wherein:

FIG. 2 shows diagramatically the measuring transducer with associated probe;

FIG. 3 shows on a larger scale the distal probe part of the measuring transducer;

DESCRIPTION OF THE PREFERRED EMBODIMENTS

EXAMPLE 1

Figure 1:
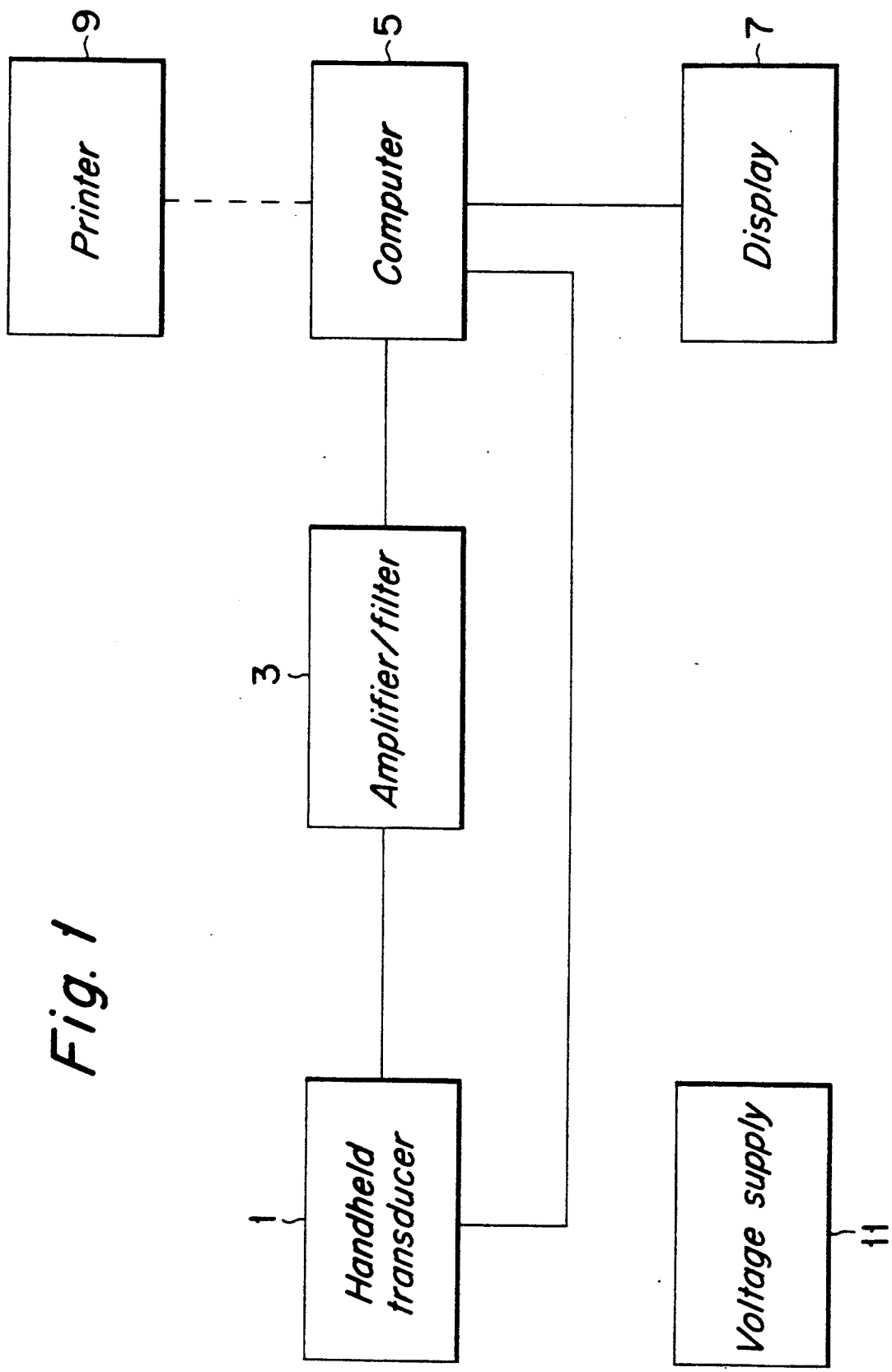
FIG. 1 shows diagramatically the construction of an apparatus according to the present invention with its auxiliary equipment.

FIG. 1 shows diagrammatically the structure of the instrument in the form of a block diagram. In principle, the instrument consists of a manually held measuring transducer 1, which via a cable is connected to a recording unit consisting of an amplifier with filter 3, computer 5, display 7, printer 9 and a device 11 for voltage supply. In the amplifying unit 3 the amplification is adjusted in such a manner that a suitable signal size is obtained to computer 5. Said computer 5 is of a conventional type and can be constituted for example by a Zilog Z80 with associated operational circuits and programable memory. In this non-limiting example there has been chosen as a display 7 a liquid crystal display, since such device consume substantially less energy than a corresponding display of the light emitting diode type. If, however, the instrument is directly mains-connected this latter type of better readability can advantageously be used.

The voltage supply unit 11 may consist of a rechargable system with nickel-cadmium cells and associated charger. However, the instrument may also be connected directly to the mains. In both cases the voltage unit contains suitably arranged control circuits stabilizing the voltage through the other part of the electronic equipment.

In FIGS. 2 and 3 the manually held measuring probe 1 is shown more in detail. The measuring probe 1 in principle consists of a probe 13 attached to a handle 15 and the free distal end 17 which is shown in enlargement in FIG. 3. This free end 17 is at its tip provided with a temperature sensor or transducer 19 which through electrically leading cables 21 is connected with the recording unit of the instrument as described in connection with FIG. 1. The free end 17 of the probe 13 is further provided with markings 23 enabling measurement of the depth of the periodontal pocket.

According to FIG. 2 the measuring probe is provided with a switch for activating the instrument.

The function of the instrument described is briefly the following.

The measuring probe 1 is placed with the free end 17 of probe 13 placed in the periodontal pocket which is subject to diagnosis, sensor or transducer 19 being positioned adjacent to the bottom of the pocket. The electronics are then activated by means of a switch 25. The temperature which is registered at the bottom of the periodontal pocket is measured by the computer, and when the signal has been stabilized the level is recorded and the operator is correspondingly informed for example by a short sound signal. The measured value can then as the case may be be registered with printer 9.

Then the measuring probe 13 with its free end 17 and sensor or transducer 19 is moved to the mouth of the periodental pocket and the measuring procedure is repeated. By means of computer 5 the difference between the two temperatures measured is now calculated, said difference being shown on the display 7 of the instrument and may also be registered by printer 9.

In connection with measuring the temperature at the bottom of the periodental pocket also the depth of said pocket is measured by means of the scale or marking 23.

By correlating the temperature difference measured and the depth of the periodontal pocket information whether the periodental process is moving into an active stage and whether the process is established will be obtained in a simple manner. In accordance with the result obtained a suitable treatment regime can then be instituted.

In an alternative embodiment of the apparatus according to the invention the means for temperature measurement may comprise a probe 13 with two transducers 19,19' displaceable relative to each other. The apparatus also includes a measuring means with a graduated scale 23 for measuring the depth of the periodonal pocket, one end of the probe being permanently connected to the measuring means at its free end, whereas the other transducer 19' is movable along the scale so that the temperature difference between the bottom and the mouth of the periodontal pocket can be registered at the same time as the pocket depth is measured.

EXAMPLE 2

Figure 4:
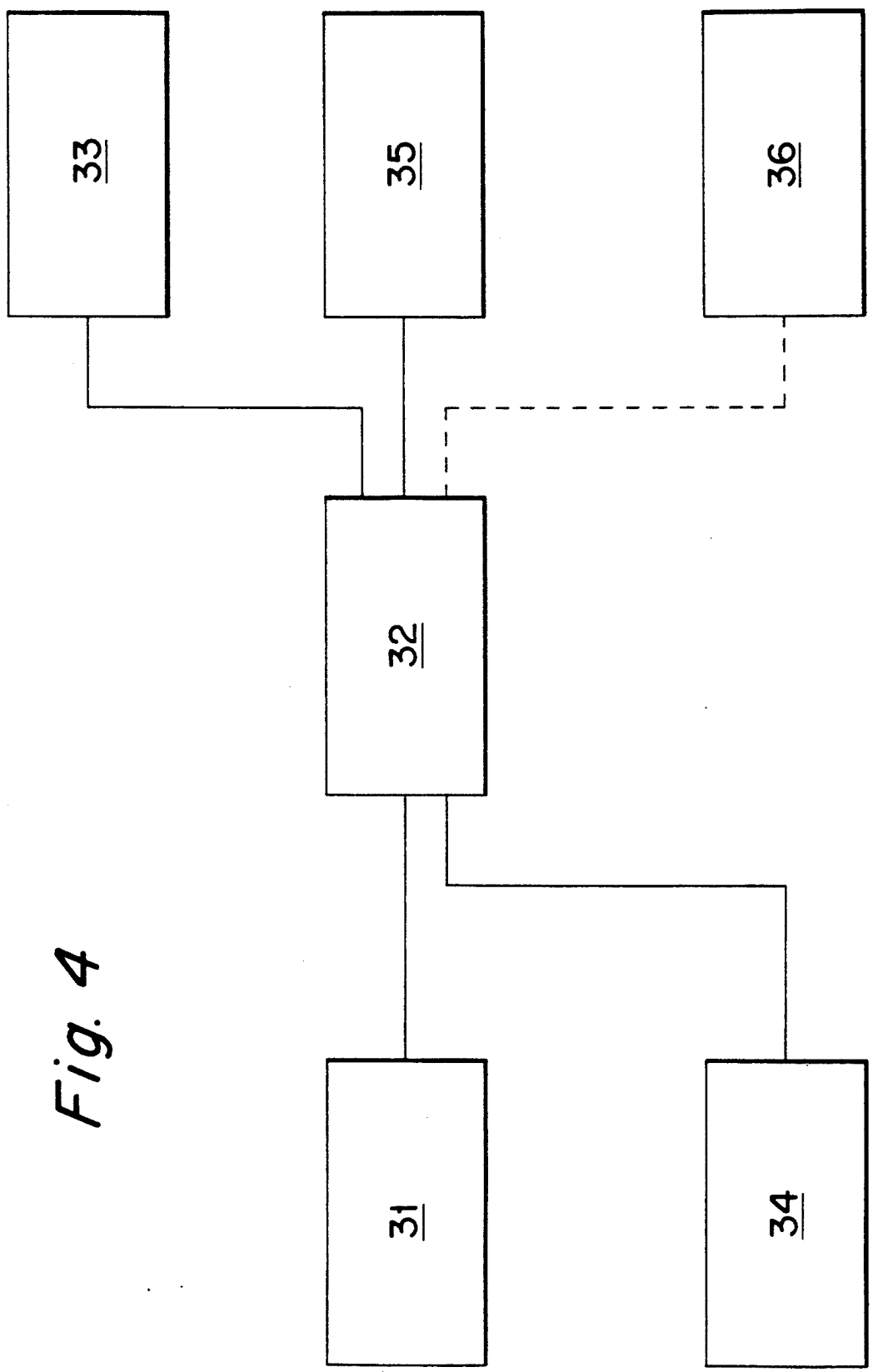
FIG. 4 shows diagrammatically a scheme on another embodiment of the invention.
Figure 5:
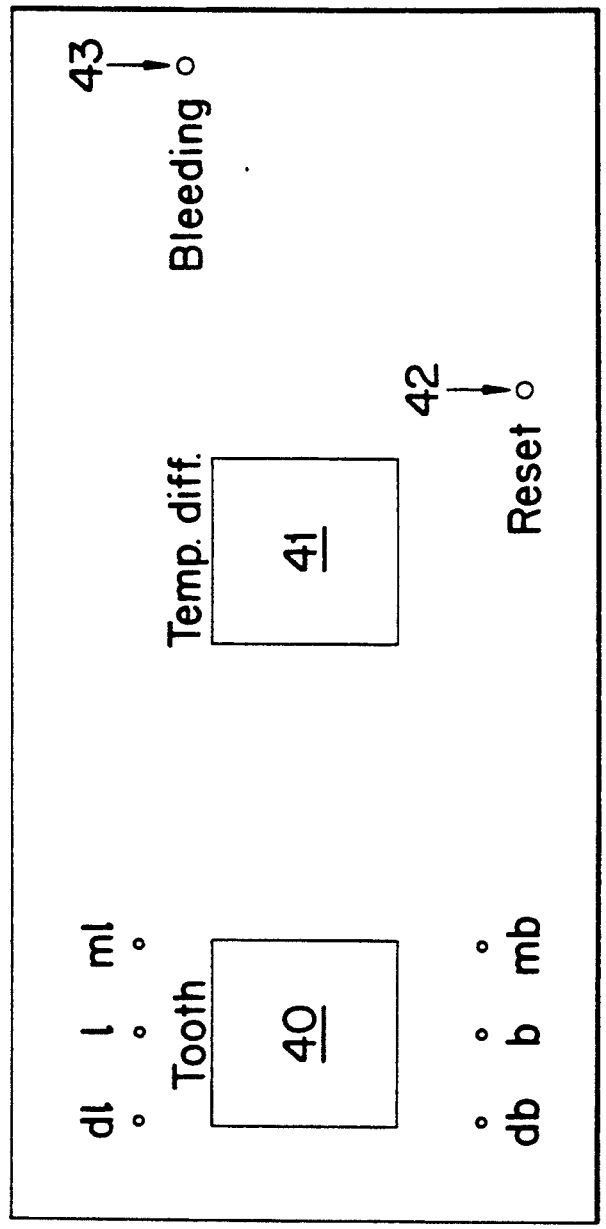
FIG. 5 shows more in detail the display unit of the embodiment of FIG. 4;-

The block diagram in FIG. 4 shows another preferred embodiment of the apparatus according to the present invention of the apparatus according to the present invention. The temperature probe with its sensor 31 is connected via a cable to an electronic unit 32 consisting of an amplifier with filter, computer and power supply. The temperature probe has a build-in-activator for registration of eventual bleeding in the tooth pocket. The display 33 unit as shown in FIG. 5 is connected via a cable to the electronic unit. The display has two groups 40,41 of figures. One 40 for indication of the number of the tooth and another 41 for the display of the temperature difference between the mouth of the periodontal pocket and the bottom. Furthermore, there is an array of indicators to show the position in the tooth pocket and a reset-switch 42 to be able to start the measurements from the beginning. The registration of the temperature is activated by a footswitch 34.

As seen in FIG. 4 a remote display 35 and/or a printer 36 is also available to connect to the electronic unit.

The measuring procedure is as follows:
1. Press the "reset" button.
2. The probe 31 is placed into the bottom of the tooth pocket.
3. Activate the footswitch 34.
4. When a low frequency signal is heard the measurement procedure is completed.
5. Move to the mouth of the tooth pocket.
6. Activate the footswitch 34.
7. When the measuring period is completed a high frequency signal is heard.
8. The display shows the temperature difference and the indicator moves automatically to the next measuring site.

Registration of bleeding can be performed for the measured position by activating the probe. An indication 43 will appear on the display.

The advantage with this embodiment is that the probe could be held more firmly since the measurement is activated by the footswitch.

EXAMPLE 3

Example of Registration Correlated to the Development of Periodontitis

Figure 6:
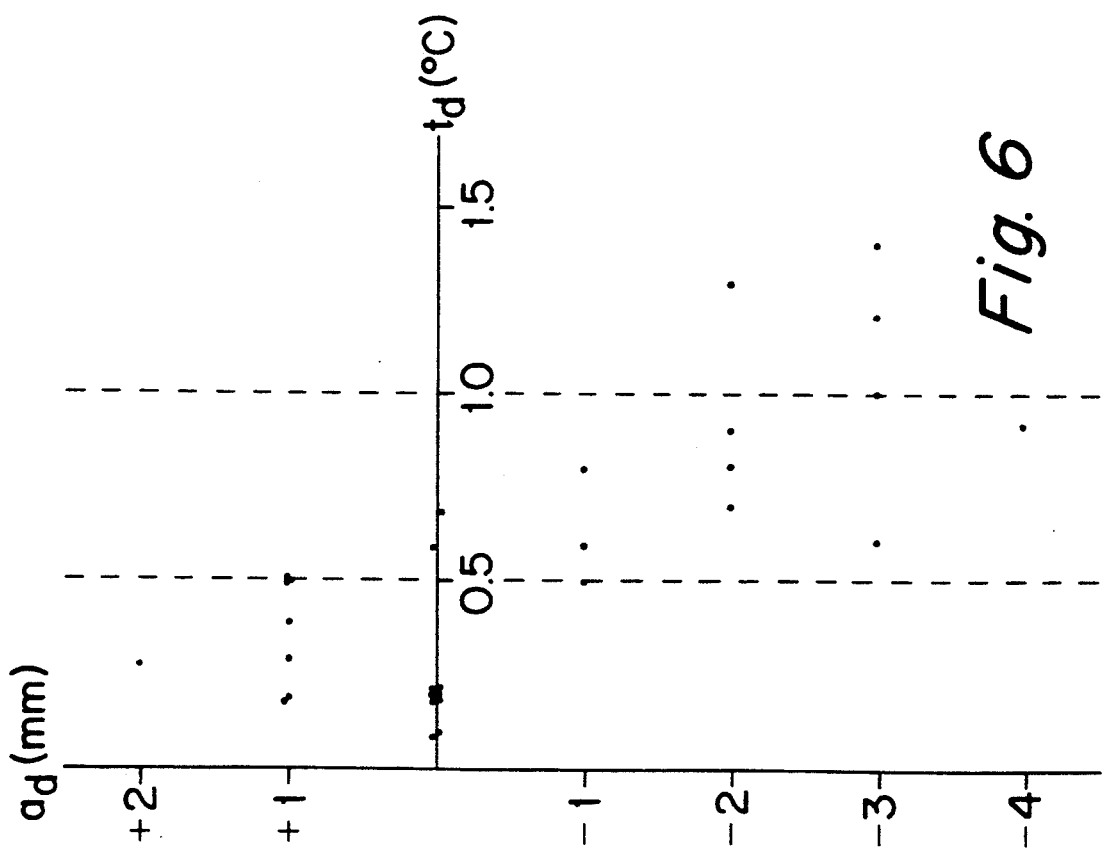
FIG. 6 shows a diagram on the development of periodontitis over time as a function of the temperature difference between the bottom and the mouth of the periodontal pocket.

FIG. 6 shows registrations of the initial temperature difference between the bottom and the mouth ($t_d$) of 30 periodontal pocket at the initial stage 30 periodontal pockets distributed among 4 patients and the subsequent change in anchorage of the tooth at the respective periodontal pocket measured after five months ($a_d$). The teeth around which the registrations have been made have all diagnosed periodontitis. A positive value of $a_d$ means that the attachment has increased, whereas a negative value means loss of attachment, i.e. the periodontitis has progressed. Values of $t_d < 0.5°$ C. in the initial stage are seen only for periodontal pockets where a gain or no change of the attachment of the tooth has been registered. Average $a_d$ in the range is 0.46 mm, i.e. a gain of attachment. Values of $t_d \leq 0.5°$ C. but $< 1.0°$ C. have often resulted in a loss of tooth attachment. Average $f_d$ in said range is $-1.00$ mm. The most serious losses of tooth attachment are seen for $t_d \geq 1.0°$ C. having an average $a_d$ in the range of $-2.75$ mm, i.e. the periodontitis has developed.

EXAMPLE 4

Figure 7:
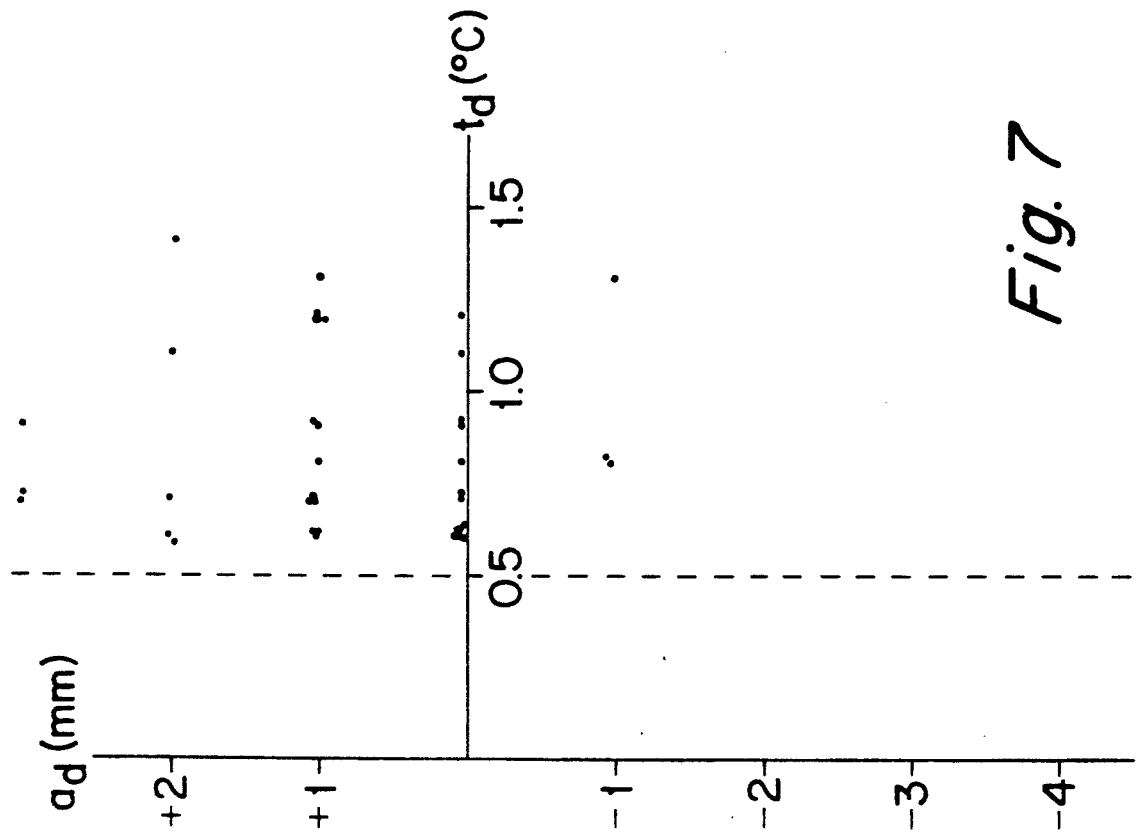
FIG. 7 shows a corresponding diagram including the result of hygiene treatment.

FIG. 7 shows registrations of the initial temperature difference between the bottom and the mouth of 35 periodontal pockets ($t_d$) distributed among 6 patients and the subsequent change in anchorage of the tooth at the respective peridontal pocket ($a_d$) measured after 2 months. Only periodontal pockets with a temperature difference of more than $0.5°$ C. ($t_d > 0.5°$ C.) were selected. After registration of $t_d$, they were given hygiene treatment with subgingival scaling. After 2 months change in periodontal anchorage was registered ($a_d$). By the treatment these periodontal pockets, which would have lost periodontal attachment according to Example 3 because of active periodontitis as Indicated by $t_d > 0.5°$ C. instead gained or maintained their original level of anchorage, as an average $a_d = 0.77$ mm.

We claim:

1. A process for diagnosing an inflammatory condition related to periodontitis based on conditions around a periodonal pocket, comprising the steps of:
    a) measuring a distance between the bottom and the mouth a periodontal pocket;
    b) measuring a temperature difference between the bottom and the mouth of the periodontal pocket; and
    c) determining the degree and development of the periodontitis based on the measurements taken under step a) and step b).

2. A process for diagnosing an inflammatory condition related to periodontitis based on conditions around a periodonal pocket according to claim 1, comprising the further step of establishing the stage of activity of said periodontitis based on the determination of said determining step.

3. Apparatus for diagnosing an inflammatory condition related to periodontitis, comprising:
    means having a graduated scale for measuring depth of a periodontal pocket;
    means for measuring a temperature difference between a bottom and a mouth of a periodontal pocket, said means for temperature comprising a probe having two sensors movable relative to each other, one sensor of the probe being permanently connected to the depth measuring means at a free end, the other sensor of the probe being movable along the scale so that the temperature difference between the bottom and the mouth of the periodontal pocket can be recorded at the same time as the pocket depth is measured; and
    means for recording said temperature difference between the bottom and the mouth of the periodontal pocket measured by said measuring means.

4. Apparatus according to claim 3, wherein the probe comprises two sensors selected from a group consisting of thermoelement, thermistor, semiconductor diode and resistance transducer.

* * * * *